United States Patent
Shan et al.

(10) Patent No.: US 10,588,712 B2
(45) Date of Patent: Mar. 17, 2020

(54) MOVEABLE INTERFACE BETWEEN A STEPPER AND A STABILIZER

(71) Applicant: Focal Healthcare Inc., Toronto, Ontario (CA)

(72) Inventors: Dandan Shan, London (CA); Jeffrey Bax, London (CA); Chicuong La, Toronto (CA)

(73) Assignee: Focal Healthcare Inc., Toronto, Ontario (CA)

( * ) Notice: Subject to any disclaimer, the term of this patent is extended or adjusted under 35 U.S.C. 154(b) by 0 days.

(21) Appl. No.: 15/755,504

(22) PCT Filed: Aug. 26, 2016

(86) PCT No.: PCT/CA2016/051015
§ 371 (c)(1),
(2) Date: Feb. 26, 2018

(87) PCT Pub. No.: WO2017/031600
PCT Pub. Date: Mar. 2, 2017

(65) Prior Publication Data
US 2018/0243048 A1    Aug. 30, 2018

Related U.S. Application Data

(60) Provisional application No. 62/210,637, filed on Aug. 27, 2015.

(51) Int. Cl.
*A61B 90/50* (2016.01)
*A61B 34/30* (2016.01)
(Continued)

(52) U.S. Cl.
CPC .............. *A61B 90/50* (2016.02); *A61B 8/085* (2013.01); *A61B 8/0841* (2013.01); *A61B 8/12* (2013.01);
(Continued)

(58) Field of Classification Search
CPC ... A61B 90/50; A61B 17/3403; A61B 8/4218; A61B 8/0841; A61B 8/085; A61B 8/483;
(Continued)

(56) References Cited

U.S. PATENT DOCUMENTS

| 4,567,782 A | 2/1986 | Speicher et al. |
| 4,930,598 A | 6/1990 | Murrill et al. |

(Continued)

FOREIGN PATENT DOCUMENTS

| EP | 1843713 A1 | 10/2007 |
| EP | 1962711 | 9/2008 |

(Continued)

OTHER PUBLICATIONS

Supplementary European Search Report in corresponding European Application No. EP 16 83 8178, dated Mar. 7, 2019.

*Primary Examiner* — Victor L MacArthur
(74) *Attorney, Agent, or Firm* — Knobbe, Martens, Olson & Bear, LLP

(57) ABSTRACT

A compound rotational interface and stepper assembly, the assembly including: a stepper supporting linear, rotational or both linear and rotational motion on a longitudinal axis; a compound rotational interface including a compound pinned parallelogram in a scissor arm arrangement bound by a first end coupled to a base and a second end coupled to a first rotational joint, the first rotational joint coupled to the stepper; the compound pinned parallelogram moveable from a first linear position to a second linear position and the first rotational joint moveable from a first angular position to a second angular position; and a linear direction defined by the compound pinned parallelogram substantially perpendicular to an axis of rotation defined by the first rotational joint.

23 Claims, 9 Drawing Sheets

(51) Int. Cl.
  *A61B 10/02* (2006.01)
  *A61B 8/12* (2006.01)
  *A61B 8/00* (2006.01)
  *A61B 8/08* (2006.01)
  *A61B 17/34* (2006.01)
  *A61B 34/20* (2016.01)
  *A61B 90/00* (2016.01)
  *A61B 10/04* (2006.01)

(52) U.S. Cl.
  CPC ............ *A61B 8/4218* (2013.01); *A61B 8/466* (2013.01); *A61B 8/483* (2013.01); *A61B 10/0241* (2013.01); *A61B 17/3403* (2013.01); *A61B 34/30* (2016.02); *A61B 2010/045* (2013.01); *A61B 2017/3413* (2013.01); *A61B 2034/2059* (2016.02); *A61B 2090/3784* (2016.02); *A61B 2090/506* (2016.02); *A61B 2090/508* (2016.02); *A61B 2090/5025* (2016.02)

(58) Field of Classification Search
  CPC ....... A61B 8/466; A61B 8/12; A61B 10/0241; A61B 34/30; A61B 2010/045; A61B 2090/5025; A61B 2090/506; A61B 2017/3413; A61B 2090/508; A61B 2034/2059; A61B 2090/3784
  See application file for complete search history.

(56) References Cited

U.S. PATENT DOCUMENTS

| | | | |
|---|---|---|---|
| 5,397,323 A * | 3/1995 | Taylor | B25J 9/1065 606/130 |
| 5,569,013 A | 10/1996 | Evans et al. | |
| 5,817,084 A * | 10/1998 | Jensen | B25J 9/1065 606/1 |
| 5,984,408 A | 11/1999 | Bujaryn | |
| 6,289,579 B1 * | 9/2001 | Viza | B65G 47/26 29/740 |
| 6,665,554 B1 | 12/2003 | Charles et al. | |
| 6,788,018 B1 | 9/2004 | Blumenkranz | |
| 2007/0221895 A1 | 9/2007 | Pieger et al. | |
| 2010/0198063 A1 | 8/2010 | Huber et al. | |
| 2011/0306864 A1 | 12/2011 | Zarate et al. | |
| 2012/0067156 A1 | 3/2012 | Chen et al. | |
| 2012/0071752 A1 * | 3/2012 | Sewell | A61B 6/12 600/424 |
| 2012/0191107 A1 * | 7/2012 | Tanner | A61B 6/12 606/130 |
| 2014/0121501 A1 | 5/2014 | Fichtinger et al. | |

FOREIGN PATENT DOCUMENTS

| | | |
|---|---|---|
| EP | 2035193 A1 | 3/2009 |
| WO | WO 2006/016390 A1 | 2/2006 |
| WO | WO 2007/075864 A1 | 7/2007 |
| WO | WO 2007/141320 A1 | 12/2007 |
| WO | WO 2010/049483 A1 | 5/2010 |
| WO | WO 2012/082418 A1 | 6/2012 |
| WO | WO 2016/112452 A1 | 7/2016 |

* cited by examiner

MOVEABLE INTERFACE BETWEEN A STEPPER AND A STABILIZER

CROSS REFERENCE TO RELATED APPLICATIONS

This application is the U.S. National Phase of International Application No. PCT/CA2016/051015, filed Aug. 26, 2016, designating the U.S. and published in English as WO 2017/031600 A1 on Mar. 2, 2017 which claims the benefit of U.S. Provisional Patent Application No. 62/210,637 filed Aug. 27, 2015. Any and all applications for which a foreign or domestic priority claim is identified here or in the Application Data Sheet as filed with the present application are hereby incorporated by reference under 37 CFR 1.57.

BACKGROUND OF THE INVENTION

Field of the Invention

The present invention relates generally to a moveable interface between a stabilizer arm and a stepper for carrying a payload.

Description of the Related Art

A stabilizer and stepper assembly can be used in various medical settings for manipulating and positioning payloads. The stabilizer comprises one or more mechanical arms with each arm typically including multiple joints and multiple degrees of freedom of motion. Typically, stabilizers are configured to support omni-directional motion. The stepper is a platform for receiving and holding a payload, and the stepper is typically coupled at or near an end of at least one arm of the stabilizer.

In medical settings, uses of the stabilizer/stepper assembly include imaging, biopsy, therapy and surgery. As a specific example, a stabilizer/stepper assembly used for Transrectal Ultrasound (TRUS) imaging and biopsy of a prostate comprises a multiple jointed stabilizer supporting omni-directional motion connected to a stepper that holds an ultrasound transducer and a needle guide. The ultrasound transducer is typically elongate and generally tubular with a diameter sized to pass through an anal sphincter and to be received within a rectum. The stepper supports linear motion along and/or rotational motion around the longitudinal axis of the transducer. The needle guide is also typically elongate and generally tubular. The longitudinal axis of the needle guide may be substantially parallel or askew to the longitudinal axis of the transducer, and is typically constrained such that the needle is visible in the ultrasound image. For example, the longitudinal axis of the needle guide may typically be less than 45 degrees offset from the longitudinal axis of the transducer. For an end-fire transducer the needle guide is aligned in a substantially parallel orientation while for a side-fire transducer the needle guide is aligned to be offset from parallel alignment.

Several stabilizer and stepper assemblies have been suggested for TRUS imaging and/or biopsy including, for example, in U.S. Pat. No. 7,832,114 (issued 16 Nov. 2010), U.S. Pat. No. 7,604,645 (issued 20 Oct. 2009), U.S. Pat. No. 6,248,101 (issued 19 Jun. 2001), U.S. Pat. No. 5,961,527 (issued 5 Oct. 1999), and U.S. Pat. No. 5,931,786 (issued 3 Aug. 1999). However, these suggested assemblies as well as current commercially available assemblies suffer from an inability to navigate challenges presented by the anal and rectal anatomy during TRUS imaging and biopsy of the prostate. Specifically, the anal sphincter and rectal cavity of an adult male easily allows alignment of the transducer and needle guide with a basal to medial portion of the prostate, but not with the medial to apical portion of the prostate. These anatomical challenges can be complicated by anal or rectal pathology or abnormalities such as fissures, growths or swellings, and may be further complicated by patient movement during an imaging or biopsy event.

Accordingly, there is a continuing need for alternative stabilizer and stepper assemblies.

SUMMARY OF THE INVENTION

In an aspect there is provided, a stabilizer and stepper assembly for performing a medical procedure, the assembly comprising:
a stabilizer comprising a plurality of joints supporting multi-directional motion;
a stepper for holding an elongate medical instrument having a longitudinal axis, the stepper supporting linear, rotational or both linear and rotational motion of the medical instrument on its longitudinal axis;
a compound rotational interface operably connected to the stabilizer and the stepper;
the compound rotational interface comprising a compound pinned parallelogram in a scissor arm arrangement bound by a first end coupled to the stabilizer and a second end coupled to a first rotational joint, the first rotational joint coupled to the stepper;
the compound pinned parallelogram moveable from a first linear position to a second linear position and the first rotational joint moveable from a first angular position to a second angular position; and
a linear direction defined by the compound pinned parallelogram substantially perpendicular to an axis of rotation defined by the first rotational joint, and the axis of rotation substantially perpendicular to the longitudinal axis of the medical instrument.

In another aspect there is provided a compound rotational interface and stepper assembly, the assembly comprising:
a stepper supporting linear, rotational or both linear and rotational motion on a longitudinal axis;
a compound rotational interface comprising a compound pinned parallelogram in a scissor arm arrangement bound by a first end coupled to a base and a second end coupled to a first rotational joint, the first rotational joint coupled to the stepper;
the compound pinned parallelogram moveable from a first linear position to a second linear position and the first rotational joint moveable from a first angular position to a second angular position; and
a linear direction defined by the compound pinned parallelogram substantially perpendicular to an axis of rotation defined by the first rotational joint.

In yet another aspect there is provided a compound rotational interface device comprising:
a parallelogram linkage bound by a first end coupled to a base and a second end coupled to a bracket supporting a first rotational joint;
the parallelogram linkage providing a first degree of freedom and the first rotational joint providing a second degree of freedom; and
a linear direction of motion defined by the parallelogram linkage substantially perpendicular to an axis of rotation defined by the first rotational joint.

In still another aspect there is provided a rotational adaptor for a scissor arm comprising:

a U-shaped bracket coupled to first and second pivot joints along a longitudinal axis of a scissor arm;

the U-shaped bracket comprising a base arm and two side arms;

the two side arms pivotally coupled to the first pivot joint and at least one arm of the two side arms slidably coupled to the second pivot joint;

the base arm housing a rotational joint for supporting a payload.

In further aspects, the assembly or device is incorporated in computer implemented systems or methods of detecting unintended patient movement.

DETAILED DESCRIPTION OF PREFERRED EMBODIMENTS

Figure 1:
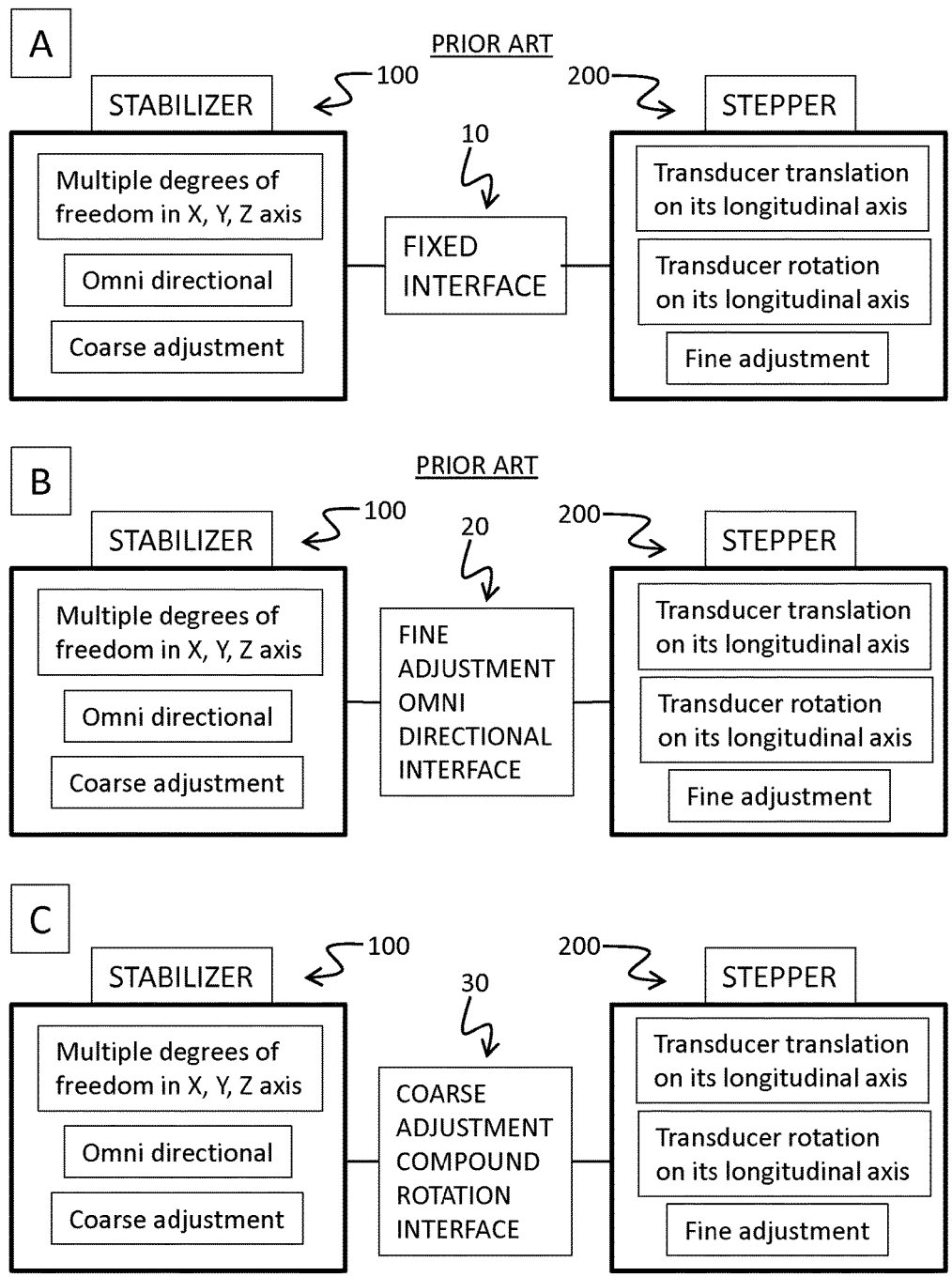
FIGS. 1A to 1C show block diagram representations of various stabilizer/stepper assemblies.

Referring to the drawings, FIGS. 1A and 1B show block diagram representations of various stabilizer/stepper assemblies suggested for TRUS imaging and/or biopsy for prostate. FIG. 1A shows a stabilizer 100 comprising multiple moveable joints providing multiple degrees of freedom supporting omni-directional coarse adjustment of an ultrasound transducer held by a stepper 200 from a position outside and near to an exterior surface of an anal orifice of a patient to a position inserted through an anal sphincter and within a rectal cavity of the patient. Post-insertion the stabilizer joints are locked to prevent any motion of the stabilizer. Post-insertion the transducer position may be adjusted using fine adjustment mechanisms provided by the stepper 200, for example linear motion along and/or rotational motion around a longitudinal axis of the transducer. The stepper 200 is connected to the stabilizer 100 through a fixed interface. Therefore, a desired position movement post-insertion that cannot be accommodated by fine adjustments of the stepper 200 must be accomplished by unlocking the stabilizer 100 and moving the transducer to the desired position. However, the stabilizer 100 is intended for multi-directional coarse adjustments that are not suited for post-insertion movements to access a plurality of desired positions.

FIG. 1B shows a suggested implementation of a stabilizer/stepper assembly comprising the stabilizer 100 connected to the stepper 200 through an omni-directional interface 20 that supports omni-directional fine adjustments. The stabilizer/stepper assembly diagrammed in FIG. 1B improves over the stabilizer/stepper assembly shown in FIG. 1A in that post-insertion movements of the transducer to access a plurality of desired positions may be supported by omni-directional fine adjustments. However, fine adjustment mechanisms have a limited useful or practical range, as user manipulation of the fine adjustment mechanism becomes time consuming and cumbersome to achieve a large range of motion by the small increments inherent to the fine adjustment mechanism. Therefore, positional movements outside the range of the fine adjustment of the interface 20 would again require the stabilizer 100 to be unlocked to move the transducer to a desired position. Furthermore, operation of the omni-directional interface 20 is unnecessarily complicated by the multiple linear and rotational movement options that constitute the omni-directional fine adjustments.

FIG. 1C shows a stabilizer/stepper assembly comprising the stabilizer 100 connected to the stepper 200 through a compound rotational interface 30 that supports rotational coarse adjustments around a first axis that is perpendicular to the longitudinal axis of the transducer and linear coarse adjustments along a second axis that intersects the longitudinal axis of the transducer. The stabilizer/stepper assembly shown in FIG. 1C overcomes the deficiencies of the stabilizer/stepper assemblies shown in FIGS. 1A and 1B by providing for post-insertion coarse adjustments with at least 2 degrees of freedom (DOF) to access a plurality of desired positions for the prostate without needing to unlock the stabilizer. Providing a coarse adjustment mechanism at the interface ensures a sufficient range of motion to pan across the plurality of desired positions for accessing the prostate. Restricting the motion to a rotational motion around an axis perpendicular to the longitudinal axis simplifies operation of the compound rotation interface 30 by limiting options of actuating motion to a path relevant to the plurality of desired positions.

Figure 2:
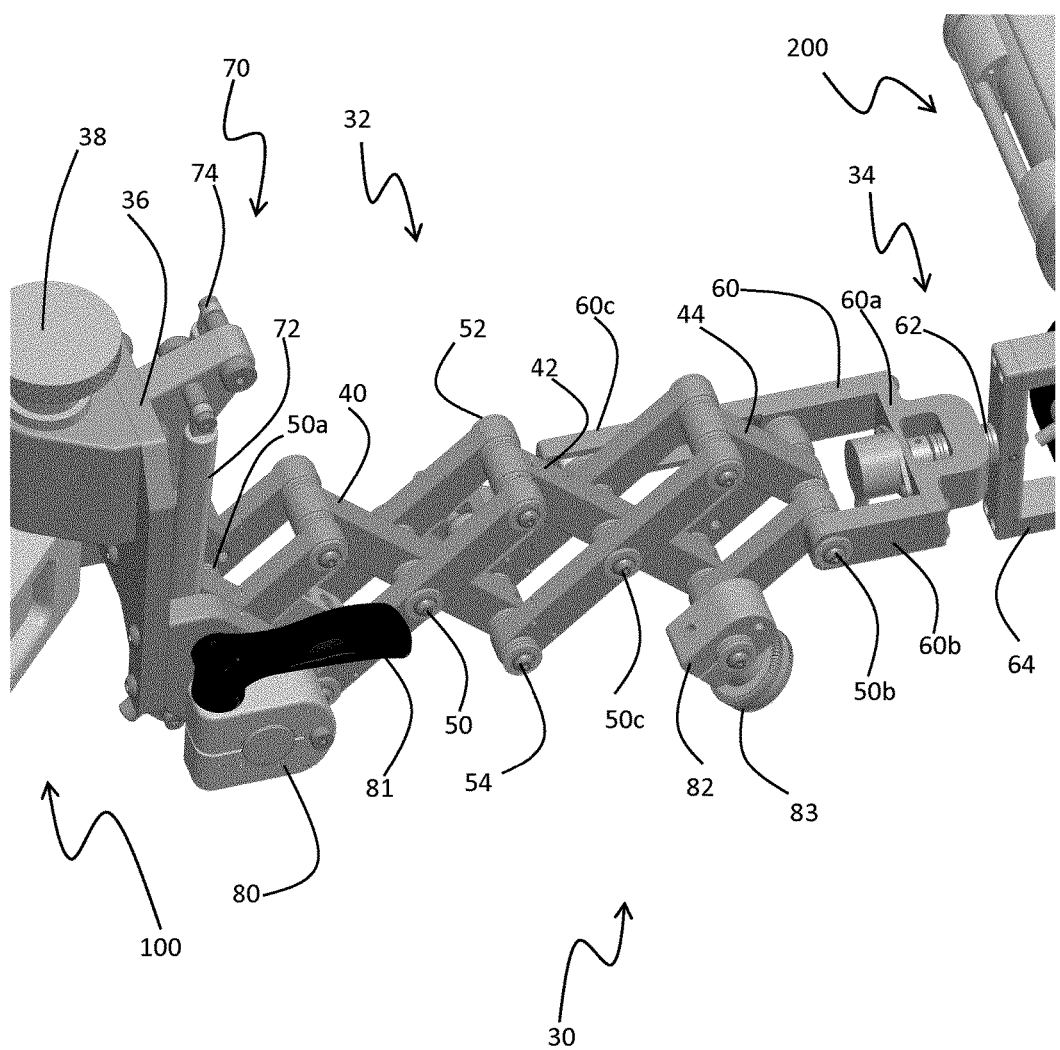
FIG. 2 shows a first perspective view of a compound rotational interface that can be connected to a stabilizer/stepper assembly.

FIGS. 2 to 5 show perspective views of a compound rotational interface 30 that may be connected to a stabilizer/stepper assembly. FIG. 2 shows a partial view of a stabilizer 100 and a partial view of a stepper 200 connected by the compound rotational interface 30, while FIGS. 3 to 5 do not show the stabilizer 100 and show a full view of the stepper 200. The compound rotational interface comprises a compound pinned parallelogram 32 in a linearly expanding/collapsing scissor arm arrangement linked to a rotational adaptor 34. The compound pinned parallelogram 32 connects to an interface base 36 that includes a bolt and bore mechanism 38 for reversibly connecting the interface base 36 to stabilizer 100. The compound pinned parallelogram 32 extends from the interface base 36 and links to rotational adaptor 34 which in turn links to stepper 200. The compound pinned parallelogram 32 provides two DOF, more specifically one DOF of linear motion along its longitudinal dimension and a second DOF of rotational motion on rotational joint 50a providing a pivot point coupling to the base 36. The rotational adaptor 34 provides two DOF, more specifically a first DOF of rotational motion on rotational joint 62 pivotally pinning symmetric U-bracket 64 to asymmetric U-bracket 60, and a second DOF of rotational motion on rotational joint 66 pivotally pinning a base block 218 of stepper 200 to symmetric U-bracket 64. The axis of rotation of rotational joint 62 (may be considered a pitch axis) is perpendicular to the axis of rotation of rotational joint 66 (may be considered a yaw axis), and the pitch axis of rotational joint 62 intersects the longitudinal rotational axis (may be considered a roll axis) of stepper 200 throughout its range of motion, while the yaw axis of rotational joint 66 remains perpendicular to the longitudinal rotational axis (roll axis) of stepper 200 throughout its range of motion. The pitch axis of rotational joint 62 can be perpendicular to the longitudinal rotational axis (roll axis) of stepper 200 at a single point or position in the range of motion, for example a central point or position in the range of motion of the stepper 200 of the yaw axis provided by rotational joint 66. The stepper 200 provides an additional two DOF, a first DOF of rotational motion along a longitudinal axis, and a second DOF of linear translational motion along the longitudinal axis. Thus, combined together the compound pinned parallelogram 32, the rotational adaptor 34, and the stepper 200 provide six DOF. Table 1 provides a summary of the six DOF with corresponding structure/joint reference number, type of motion, functional motion of a medical instrument held in the stepper from the perspective of an operator/clinician, and tracking encoder reference number.

TABLE 1

Summary of six DOF of the stepper and compound rotational interface combination shown in FIGS. 2 to 5.

| DOF | Structure/Joint Reference Number | Motion | Corresponding probe motion, from the perspective of the user | Encoder Reference Number |
| --- | --- | --- | --- | --- |
| DOF1 | 50a | Rotational | Up/down | 90A |
| DOF2 | 32 | Linear | Left/right | 90B |
| DOF3 | 62 | Rotational | Probe pitch | 90C |
| DOF4 | 66 | Rotational | Probe yaw | 90D |
| DOF5 | 218/220 | Rotational | Probe roll | 90E |
| DOF6 | 212/214 | Linear | Towards/away | 90F |

The compound pinned parallelogram defines a longitudinal dimension that extends from its connection with the interface base 36 to its connection with rotational adaptor 34, and a lateral dimension perpendicular to the longitudinal dimension. The longitudinal dimension increases and the lateral dimension decreases as the compound pinned parallelogram 32 is moved from a collapsed position to an expanded position. Conversely, the longitudinal dimension decreases and the lateral dimension increases as the compound pinned parallelogram 32 is moved from an expanded position to a collapsed position.

The compound pinned parallelogram 32 comprises three consecutively pinned parallelograms extending from the interface base 36, proximal parallelogram 40, intermediate parallelogram 42, and distal parallelogram 44, with proximal parallelogram 40 connected to the interface base 36, distal parallelogram 44 connected to the rotational adaptor 34, and intermediate parallelogram 42 connected to both the proximal parallelogram 40 and the distal parallelogram 44. Each parallelogram comprises four bars coupled at four corners by a pivot joint. Each parallelogram is positioned to have two opposing corners aligned with the longitudinal dimension of the compound pinned parallelogram and two opposing corners aligned with the lateral dimension of the compound pinned parallelogram. Being a compound pinned parallelogram, the three parallelogram portions 40, 42, and 44 share common bars and common pivot joints.

The plurality of pivots joints pinning bars of each parallelogram may be distinguished as three types of pivot joints based on location within the scissor arm arrangement of the compound pinned parallelogram 32. A plurality of central pivot joints, for example pivot joint 50, are located centrally within the scissor arm arrangement, while a plurality of first and second peripheral pivot joints, for example pivot joints 52 and 54, respectively, are located on opposing lateral ends within the scissor arm arrangement. Each of the central 50, and first 52 and second 54 peripheral pivot joints maintains longitudinal alignment with neighboring central, and first and second peripheral pivots joints, respectively as the compound pinned parallelogram 32 moves from a contracted position to an expanded position, or vice versa.

At a distal end of the compound pinned parallelogram 32, distal parallelogram 44 is coupled to rotational adaptor 34. Rotational adaptor 34 comprises an asymmetric U-bracket 60 comprising a base arm 60a and opposing arms, short arm 60b and long arm 60c extending an asymmetrical length from the base arm. Asymmetric U-bracket 60 is coupled to two neighboring central pivot points 50b and 50c that are diametrically opposing central pivots of distal parallelogram 44 aligned along a longitudinal direction of the compound pinned parallelogram 32. Central pivot joints 50b and 50c are separated by a longitudinal distance along the longitudinal direction of the compound pinned parallelogram 32, and asymmetric U-bracket 60 is pivotally pinned to the distal central pivot joint 50b closest to the U-bracket base 60a and furthest from the interface base 36 and slidably coupled to the neighboring central pivot joint 50c. More specifically, both opposing arms 60b and 60c of the U-bracket 60 are pivotally coupled to the distal central pivot joint 50b, while only the long arm 60c is slidably coupled to a neighboring central pivot joint 50c. Sliding coupling of central pivot joint 50c to long arm 60c is accomplished with a car and track mechanism, the car connected to a pivot pin of pivot joint 50c, the track formed within long arm 60c, and the car slidably received within the track. Sliding coupling of central pivot joint 50c with long arm 60c may be achieved through any other suitable sliding mechanism, such as a pin and slot mechanism where a pivot pin of pivot joint 50c is slidably coupled to a slot formed within long arm 60c. The coupling of U-bracket 60 to two neighboring central pivot points 50b and 50c ensures that the axis of linear collapsing/expanding motion of the compound pinned parallelogram 32 remains constantly aligned parallel to the rotational axis of rotational joint 62 and perpendicular to the rotational axis of rotational joint 66. The rotational joint 62 is connected to the base arm 60a of the asymmetric U-bracket 60 and is also connected with the symmetric U-bracket 64 providing rotational motion of symmetric U-bracket 64 relative to asymmetric U-bracket 60. Symmetric U-bracket 64 is in turn rotationally pinned to base block 218 of stepper 200 on rotational joint 66 providing rotational motion perpendicular to both the longitudinal axis of the stepper and perpendicular to the linear collapsing/expanding motion of the compound pinned parallelogram 32.

One or more encoders may be used to track one or more of the six DOF provided by the combination of the compound rotational interface 30 and stepper 200. In applications where positional tracking is critical all six DOF can be independently tracked by encoders. The relationship of encoders 90A to 90F to structures and/or joints is summarized in Table 1 above and shown in FIGS. 3 and 4.

A counterbalance mechanism 70 supports the central pivot joint 50a of the compound pinned parallelogram 32 that is pivotally coupled to the interface base 36, and is configured to support the combined weight of the compound rotational interface 30, stepper 200 and stepper payload such as ultrasound transducer 210. Thus, the counterbalance mechanism supports the combined weight and the resulting torque on central pivot joint 50a while the compound pinned parallelogram 32 is unlocked making it easier for operators to manipulate a payload. In optimized implementations the counterbalance mechanism maintains a rotational position (i.e., prevents a rotational drift) of central pivot joint 50a when unlocked and unsupported by the operator (e.g., physician/clinician). The counterbalance mechanism 70 comprises two force generating members, such as first gas spring 72 and second gas spring 74 connected in two different orientations from the interface base 36 to two different eccentric contact points relative to central pivot joint 50a. Each spring acts on a different linkage bar extending from proximal parallelogram 40 to counterbalance the combined weight of the rotational interface 30 and stepper 200 and associated payload. There is no fixed angular relationship between the two springs.

Figure 3:
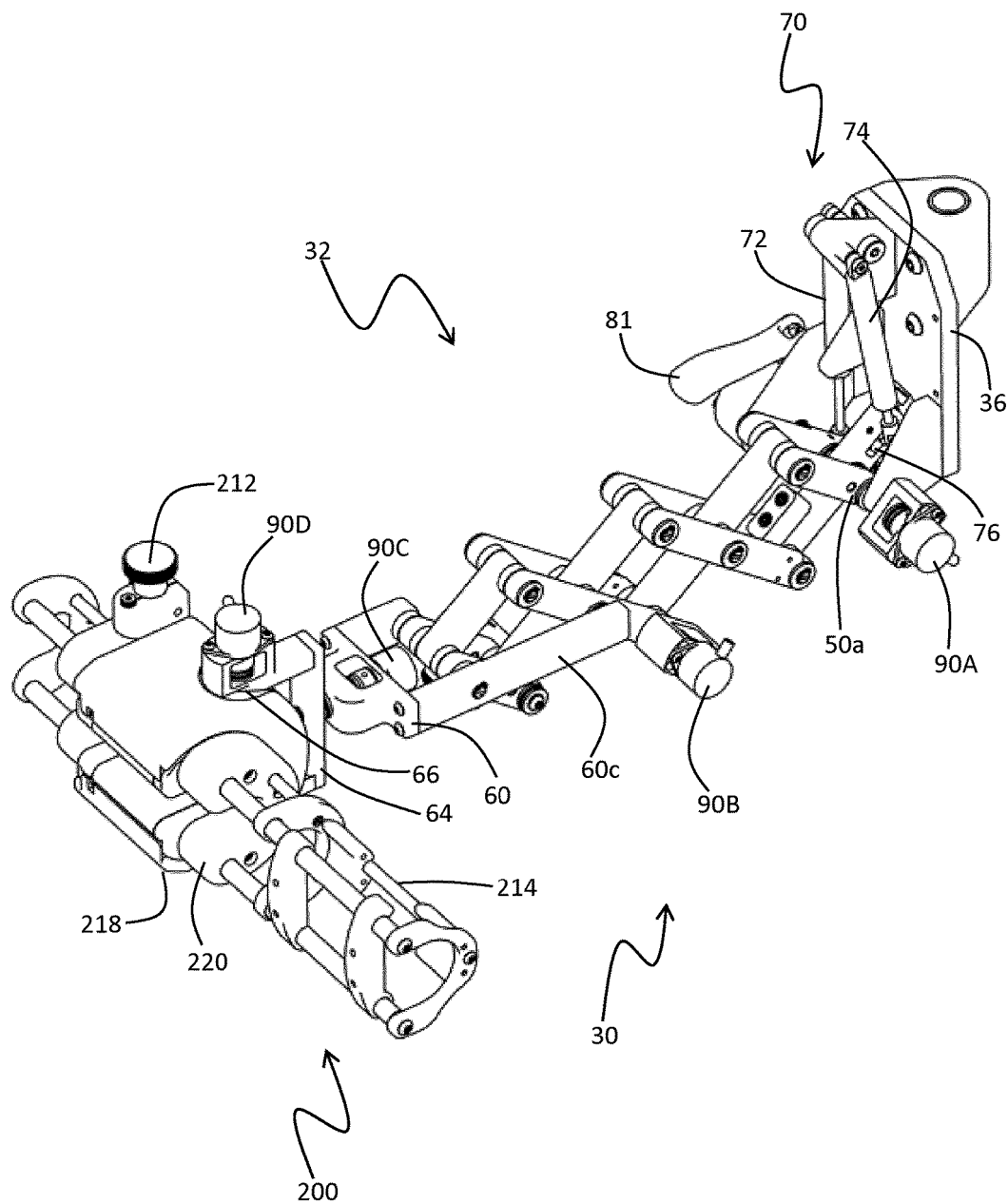
FIG. 3 shows a second perspective view of the compound rotational interface shown in FIG. 2.
Figure 4:
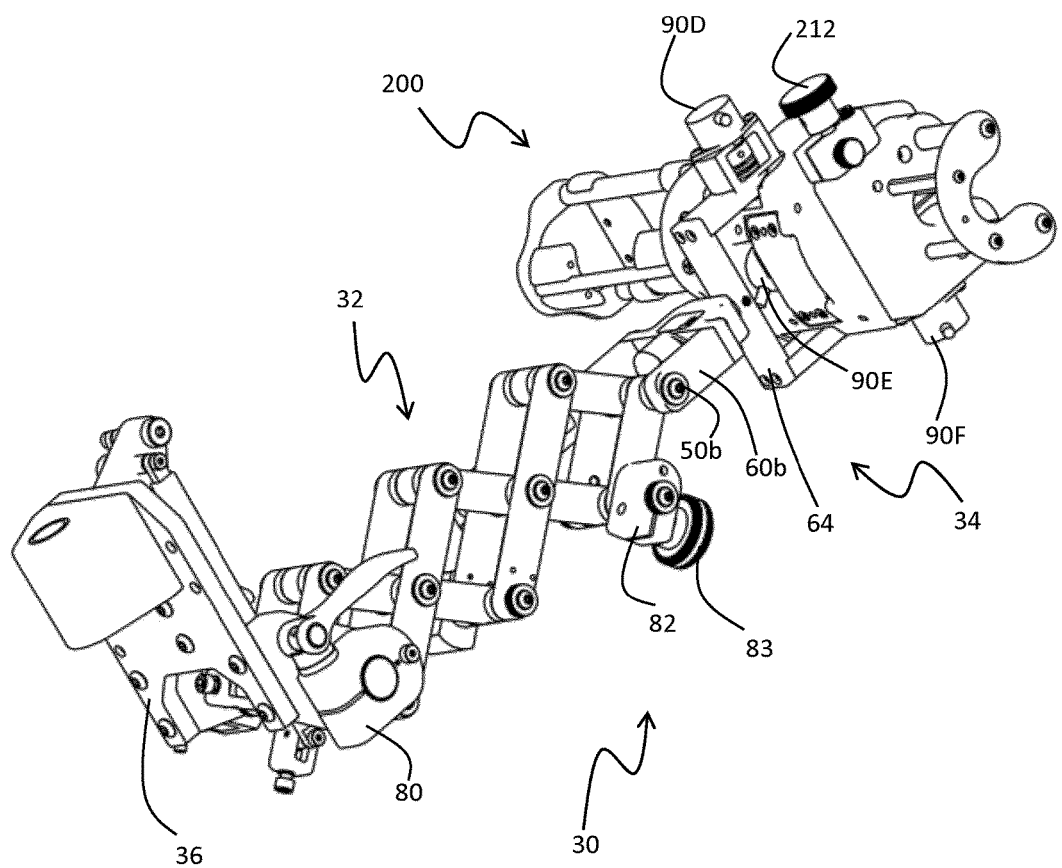
FIG. 4 shows a third perspective view of the compound rotational interface shown in FIG. 2.

As shown in FIG. 3, the longitudinal axis of each spring forms a force triangle with each of the two linkage bars pinned by pivot joint 50a. The three vertices of the force triangle are: (1) contact point of spring with base 36; (2) contact point of spring with linkage bar at a distance from pivot joint 50a; and (3) pivot joint 50a. The spring is coupled to the base and linkage bar such that the distance between the spring pivots is constrained to be equal to the compression of the spring and the size of the force triangle determines the carrying/supporting capacity of the counterbalance. For example, the size of the force triangle and consequently the carrying/supporting capacity may be adjusted by adjusting the distance between the pivot joint 50a and a contact point of the spring with a linkage bar by adjusting and reversibly locking the position of the contact point along slot 76 formed in the linkage bar. Further elaboration of a counterbalance mechanism is provided in co-pending International Patent Application No. PCT/CA2015/000023 filed 14 Jan. 2015 (Publication No. WO/2016/112452 published 21 Jul. 2016).

Two brakes are coupled to the compound pinned parallelogram 32, a first brake clamp 80 is used to lock rotational motion on central pivot joint 50a and a second brake clamp 82 is used to lock linear collapsing/expanding motion. Both brake clamps 80 and 82 may be independently manually manipulated to be changed from a first unlocked position to a second locked position. Handle actuator 81 coupled to brake clamp 80 can be manually manipulated to apply a compressive load across brake clamp 80 to lock rotational motion on central pivot joint 50a, controlling switching of the central pivot joint 50a from a motion mode to a locked mode. Knob actuator 83 can be manually manipulated to apply a compressive load across brake clamp 80 to lock linear collapsing/expanding motion of the compound pinned parallelogram 32, controlling switching of the compound pinned parallelogram 32 from a motion mode to a locked mode.

Figure 5:
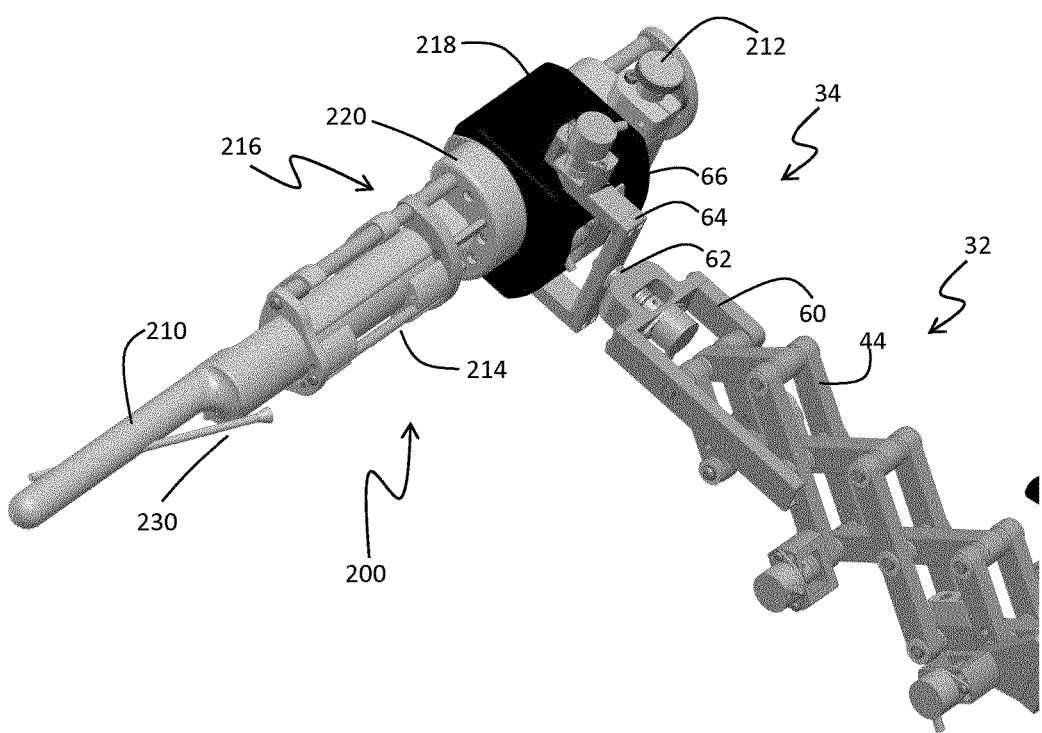
FIG. 5 shows a fourth perspective view of the compound rotational interface shown in FIG. 2.

In TRUS imaging and biopsy the stepper 200 holds an ultrasound transducer 210 as shown in FIG. 5. A needle guide 230 may be reversibly coupled to the ultrasound transducer 210—for example, the needle guide 230 may comprise a semi-circular clip (not shown) that can be used to reversibly engage a cylindrical probe portion of the ultrasound transducer 210. The ultrasound transducer 210 can be moved linearly/translationally back and forth along a longitudinal axis by manipulating an actuator knob 212 to provide one DOF. The ultrasound transducer 210 can also rotate or roll on its longitudinal axis to provide another DOF. The linear motion is provided by a rack and pinion mechanism comprising a rack formed on a peripheral centrally located and longitudinally oriented rack rod 214 of carriage 216. Carriage 216 receives and captures transducer 210 and the longitudinal axis of carriage 216 is substantially co-axial with the longitudinal axis of the transducer 210. The longitudinal axis of rack rod 214 is substantially parallel but spaced from the longitudinal axis of carriage 216. The rack rod 214 engages pinion (not shown) which is connected to and co-axial with actuator knob 212. The roll motion is provided by a revolute joint formed by semi-cylinder block 220 (centrally located along the longitudinal dimension of carriage 216) rotationally received within a half-pipe channel formed within base block 218 of stepper 200. The linear motion is tracked by the encoder 90F, while the roll motion is also tracked by the encoder 90E.

The compound rotational interface 30 defines four DOF, two mutually perpendicular axes of rotation of the rotational adaptor 34 as well as a linear collapsing/expanding motion axis and a rotational axis of the compound pinned parallelogram 32. The rotational axis of the compound pinned parallelogram 32 is perpendicular to the linear collapsing/expanding motion axis. All four DOF can be independently tracked by encoders 90A to 90D as shown in FIG. 3. The compound rotational interface 30 provides three DOF (a linear DOF of the compound pinned parallelogram 32 and two rotational DOF of the rotational adaptor 34) that substantially intersect the longitudinal axis of the ultrasound transducer 210 along its full range of motion, the three intersecting DOF providing angular motion of the transducer along a path relevant to panning across opposing peripheral points of the prostate, such as apical to basal regions or anterior to posterior regions of the prostate depending on the relative positioning of a test subject and the stabilizer/stepper assembly. The relationship of these three DOF may be further defined in that the rotational axis of joint 66 remains substantially perpendicular to the longitudinal axis of the ultrasound transducer 210 throughout its full range of motion, while the linear expanding/collapsing motion axis and the rotational axis of joint 62 are substantially perpendicular to the longitudinal axis of the ultrasound transducer 210 only when held at a center of its range of motion. As the longitudinal axis of ultrasound transducer 210 is generally configured to be parallel, and often co-axial, with the longitudinal axis of the stepper 200, the relationship of these three DOF—linear DOF of the compound pinned parallelogram 32 and two rotational DOF of the rotational adaptor 34—is generally similar with respect to both transducer 210 and stepper 200.

The compound rotational interface 30 provides angular motion of the transducer 210 while maintaining a pivot point of the transducer 210 or a remote center of motion of the stepper 200 generally aligned with the patient's anal sphincter. The maintenance of the remote center of motion is achieved by coordinated motion of two pairs of DOF, DOF of central pivot joint 50a pairs with DOF of rotational joint 62, and DOF of linear collapsing/expanding motion pairs with DOF of rotational joint 66. Furthermore, the two DOF of the rotational adaptor 34 support post-insertion tracking and adjustment to patient movement. Encoder 90C tracks motion of rotational joint 62, while encoder 90D tracks motion of rotational joint 66. Motion tracked by encoder 90C, encoder 90D, or both 90C and 90D, with an absence of or relatively lesser motion from encoders 90A and 90B is indicative of unintended patient movement. Thus, the two DOF of rotational adaptor 34 and the corresponding encoders provide a method for detecting unintended patient movement and correcting a tracking mechanism to compensate for the unintended movement. More specifically, the method comprises detection and differentiation of unintended patient movement from intended motion of the stepper directed by the physician, where unintended patient movement is indicated by activation of encoders 90D and 90C either individually or in combination, with a simultaneous absence or lack of activation or relatively lesser activation from other four encoders coupled to the compound rotational interface and the stepper. Unintended patient motion occurs more often in the patient's anterior/posterior direction in comparison to a patient's lateral direction. From the perspective of the operator, a patient's anterior/posterior direction movement is a left/right movement. This specific motion will cause rotation of rotational joint 66 without concomitant motion or with relatively lesser motion of any of the other joints/encoders than that would occur as a result of the operator intentionally moving the probe. As a result, patient movement can be detected by computer implemented tracking software and reasonably accounted for automatically. Unintended patient movement to the patient's left/right (up/down from operator's perspective) can be compensated for in a similar fashion.

Figure 6:
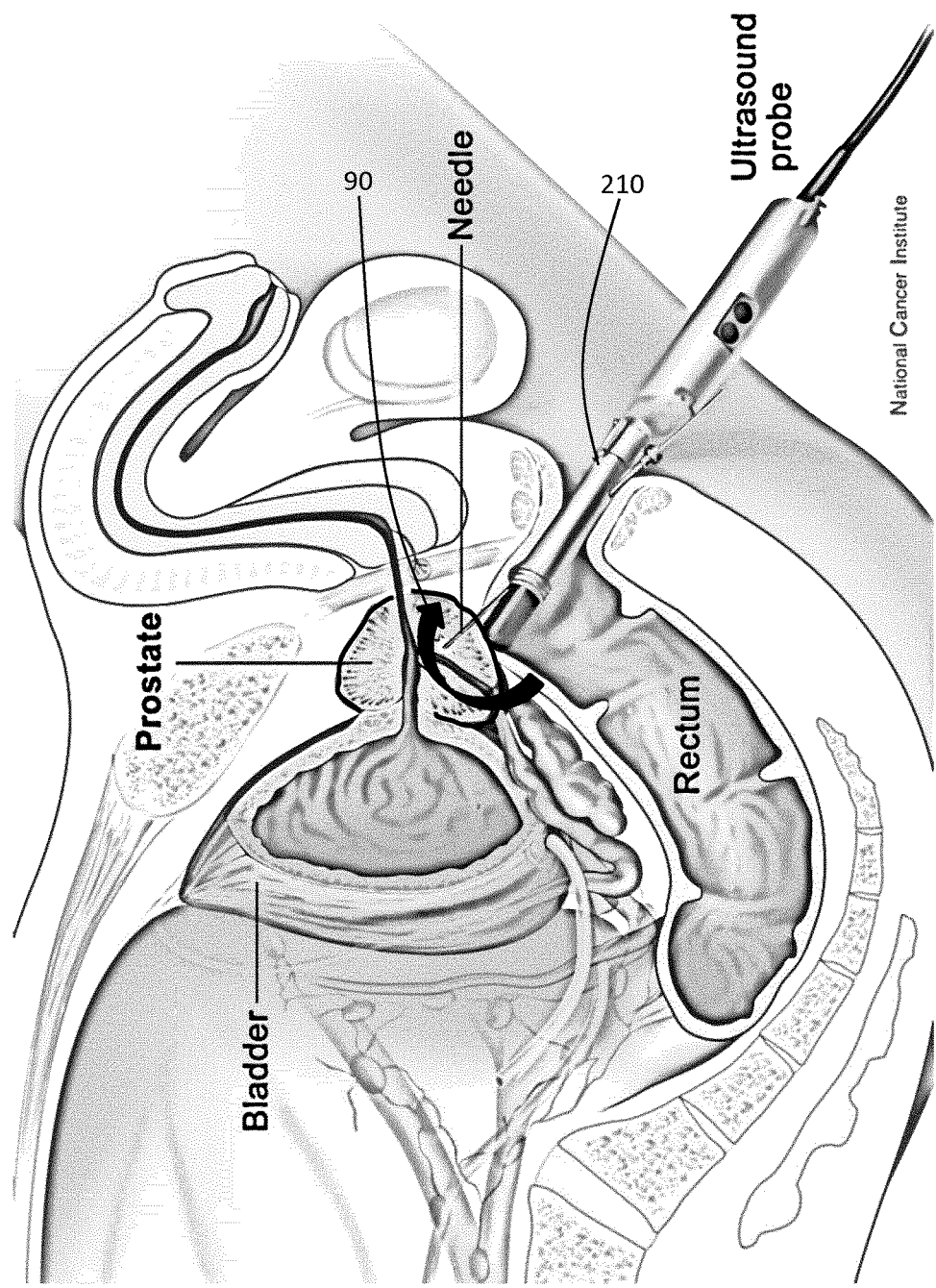
FIG. 6 shows an anatomical representation of a medical use of the compound rotational interfaces shown in FIGS. 2 to 5.

An illustrative example of using the stepper/stabilizer assembly comprising the compound rotational interface 30 is now described with respect to a TRUS imaging and/or biopsy procedure. In use, an operator, typically an urologist, initially positions the steeper 200 and the ultrasound transducer 210 held by the stepper by coarse multi-directional motion supported by the stabilizer 100. More specifically, the urologist unlocks one or more stabilizer joints and uses the coarse adjustment of the one or more stabilizer joints to position the stepper 200 so that ultrasound transducer is inserted into the rectum of a patient as shown in FIG. 6. The patient may be lying on his side or in the lithotomy position. Typically, when using a two-arm stabilizer the patient is in the lithotomy position.

FIG. 6 demonstrates that in the absence of motion along arcuate path 90 an ultrasound transducer and associated needle guide is limited by the anatomy of the rectum and anal sphincter to accessing only medial to basal portions of the prostate. Motion along arcuate path 90 is needed to access medial to apical and the anterior zone regions of the prostate. This is particularly true for enlarged prostates. A healthy human adult male prostate gland is classically described as walnut sized, having typical dimensions of 3.5 cm long from base to apex, 4.0 cm wide from left to right, and 2.5 cm deep from outer edge of peripheral zone to outer edge of anterior zone. However, biopsies are typically not performed on healthy walnut sized prostates. Rather biopsies are often times performed on enlarged prostates that may be racquet ball sized or tennis ball sized or even as large as a grapefruit. For a small sized prostate a range of motion of 10 degrees along arcuate path 90 may be sufficient to pan along the entirety of the prostate from the apical to the basal regions. However, for most enlarged prostates a 10 degree range of motion would be insufficient, and a range of motion of at least 20 degrees, more typically at least 30 degrees, along arcuate path 90 is needed to pan along most enlarged prostates from the basal to the apical region.

For convenience, the ultrasound transducer 210 is shown in FIG. 6 without the supporting stepper/stabilizer assembly. Once the ultrasound transducer 210 is inserted at a desired position within the rectum the one or more joints of the stabilizer are locked so that the stabilizer is locked and stationary. The stepper 200 is used for post-insertion fine adjustment of positioning of the ultrasound transducer 210, providing linear/translational motion along the longitudinal axis of the ultrasound transducer and/or rotational motion on the longitudinal axis. Both the linear and rotational motion may be tracked by encoders, for example encoders 90F and 90E, respectively. The compound rotational interface 30 supports a coarse adjustment of linear and angular motion of the ultrasound transducer post-insertion independent of the stabilizer 100, so that the angular motion of the ultrasound transducer 210 can be achieved along arcuate path 90 maintaining a pivot point substantially aligned with a patient's anal sphincter while the stabilizer 100 is maintained in its locked and stationary position. The urologist benefits from maintaining the stabilizer 100 locked post-insertion, as the stabilizer is awkward to manipulate and suited for multi-directional coarse adjustments up until a position of insertion within the rectal cavity, but not for post-insertion adjustments. Furthermore, the angular motion provided by the compound rotational interface 30 that allows convenient coarse adjustment panning along arcuate path 90 is very difficult, and perhaps unachievable, for many urologists to replicate using a one-armed stabilizer. Manipulation of a multi-armed stabilizer may be able to replicate motion along arcuate path 90, but is nevertheless inconvenient and impractical, and almost impossible to replicate the alignment and adherence of a remote center of motion with the patient's anal sphincter.

The compound rotational interface 30 allows for the alignment of the remote center of motion with the patient's anal sphincter to be maintained throughout unintended patient movement. The two DOF of the rotational adaptor 34 support post-insertion tracking and adjustment to patient movement. Encoder 90C tracks motion of rotational joint 62, while encoder 90D tracks motion of rotational joint 66. Motion tracked by encoder 90C, encoder 90D, or both 90C and 90D, with an absence of motion or relatively lesser motion tracked by encoders 90A and 90B is indicative of unintended patient movement. Thus, the two DOF of rotational adaptor 34 and the corresponding encoders provide a method for detecting unintended patient movement and correcting a tracking mechanism to compensate for the unintended movement. More specifically, the method comprises detection and differentiation of unintended patient movement from intended motion of the stepper directed by the physician, where unintended patient movement is indicated by activation of encoders 90D and 90C either individually or in combination, with a simultaneous absence or lack of activation or relatively lesser activation from one or more of the other four encoders coupled to the compound rotational interface and the stepper.

Typically, coarse adjustment of motion supports motion of large increments and large range of motion, while sacrificing accuracy for targeting a specific position or a specific series of positions along a path. Fine adjustment of motion achieves accuracy, while sacrificing increment and range of motion. The compound rotational interface 30 can combine benefits of accuracy with increment and range of motion by supporting a coarse adjustment of motion along an arcuate path 90 that is relevant to accessing apical to medial portions of the prostate and/or peripheral zone to anterior zone portions of the prostate as desired. The compound rotational interface 30 can achieve accuracy by constraining motion to a path relevant for panning across the prostate from the basal to the apical portion, namely an angular/rotational motion on an axis perpendicular to the longitudinal axis of the ultrasound transducer 210 while maintaining a pivot point of the transducer 210 or a remote center of motion of the stepper generally aligned with the patient's anal sphincter.

One purpose of the ultrasound transducer 210 is to image the prostate. Another purpose is to provide guidance of a biopsy guide to a region of interest—for targeted biopsy. Options for performing a targeted biopsy of the prostate include transperineal and transrectal biopsies. A transperineal biopsy requires the addition of a template which is attached to the front of a stepper device for guiding transperineal needle insertions while guidance is provided by TRUS imaging. A transrectal biopsy is most commonly performed as TRUS imaging and biopsy including a needle guide that is positioned parallel or non-parallel (e.g., skewed) of the ultrasound transducer 210 depending on the position of the transducer element within the transducer probe (e.g., end-fire position compared to side-fire position). The needle bisects the wall of the rectum into the prostate.

Several illustrative variants have been described above. Further variants and modifications are described below. Moreover, guiding relationships for configuring variants and modifications are also described below. Still further variants and modifications are contemplated and will be recognized by the person of skill in the art.

The compound rotational interface supports coarse adjustment of position. The compound rotational interface may also be adapted to support fine adjustment of position by modifying parallelogram structures or actuating mechanisms as desired.

The use of the compound rotational interface is not limited to prostate biopsies, and may find use for example in prostate imaging and prostate therapy. Additionally, the compound rotational interface may find use with other medical procedures where an elongate medical instrument having a longitudinal axis is held in a stepper/stabilizer assembly.

Figure 10:
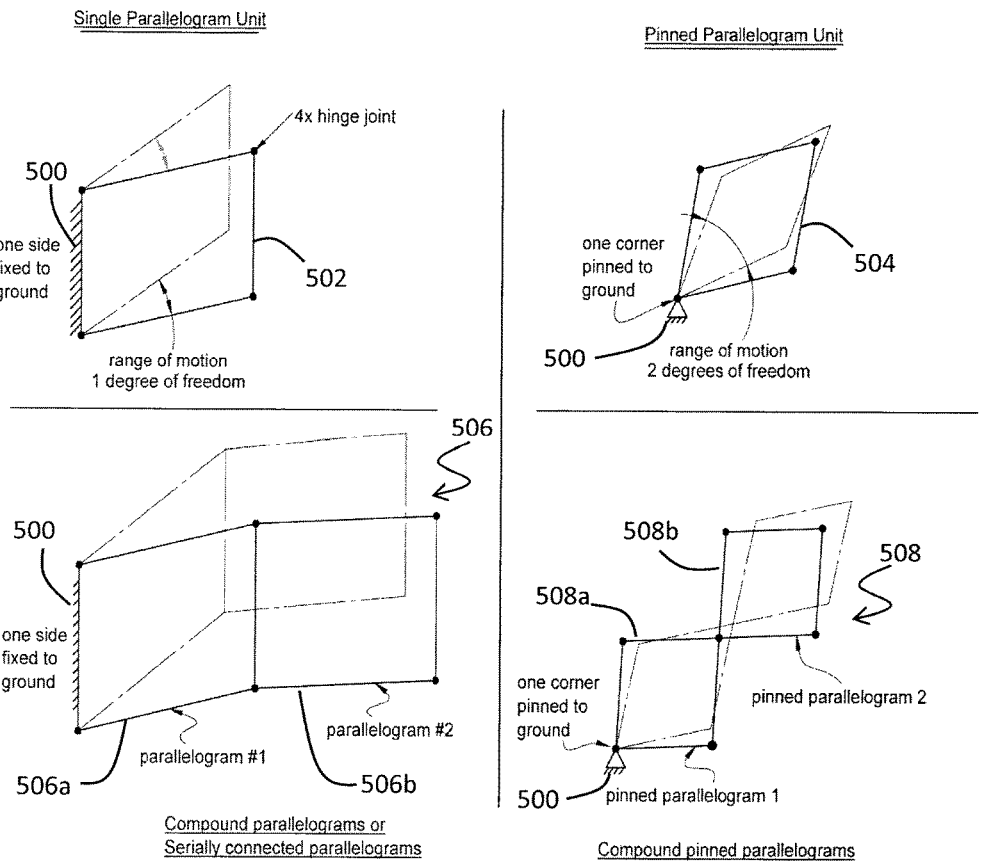
FIG. 10 shows a schematic of various illustrative parallelogram linkage structures.

The compound rotational interface may be incorporated in many conventional stepper/stabilizer assemblies including assemblies with one-armed stabilizers or multiple-armed stabilizers such as two or three armed stabilizers. Two or three armed stabilizers may allow greater flexibility for aligning the center of gravity of the stepper; for example a two arm stabilizer can carry a stepper where the center of gravity is in between two ball joints connected to the end of each arm. A three arm stabilizer can carry a stepper where the center of gravity of the stepper can be anywhere in space relative to the three arms. An example of an assembly comprising a stepper 300, compound rotational interface 130 and stabilizer 101 is shown in FIG. 10.

A compound rotational interface is generally considered to include at least one rotatable joint in combination with any other moveable joint. In examples described herein, the compound rotational interface may accommodate any variety of range of motion provided it comprises at least one linear collapsing/expanding motion axis and at least one axis of rotation, the at least one axis of rotation oriented substantially perpendicular to the linear collapsing/expanding motion axis and substantially perpendicular to the longitudinal axis of a stepper or a medical instrument held in the stepper. Motion along the at least one linear collapsing/expanding motion axis may be independent of motion on the at least one axis of rotation. Typically, the range of motion of the at least one axis of rotation is greater than about 20 degrees. Taking prostate biopsy as an example, a range of motion of at least 20 degrees is needed to pan across opposing peripheral points most enlarged prostates with respect to longitudinal or transverse dimensions of the prostate, for example panning from the apical to the basal region or from the anterior to the posterior regions of the prostate. The range of enlarged prostates encountered in the clinical setting can be diverse, ranging from slightly larger than the classic walnut sized prostate to racquetball sized, tennis ball sized and even grapefruit sized prostates. A range of motion of 180 degrees would be sufficient to accommodate almost all enlarged prostates. However, the majority of enlarged prostates may be accommodated by a smaller range of motion of 90 to 120 degrees. The range of motion can be set according to the application, but will always be greater than or equal to 10 degrees. Typically, the range of motion of the rotational interface will be greater than about 15 degrees, 20 degrees, 30 degrees, 40 degrees, 50 degrees, 60 degrees, 70 degrees or greater than or equal to any number therebetween.

Figure 7:
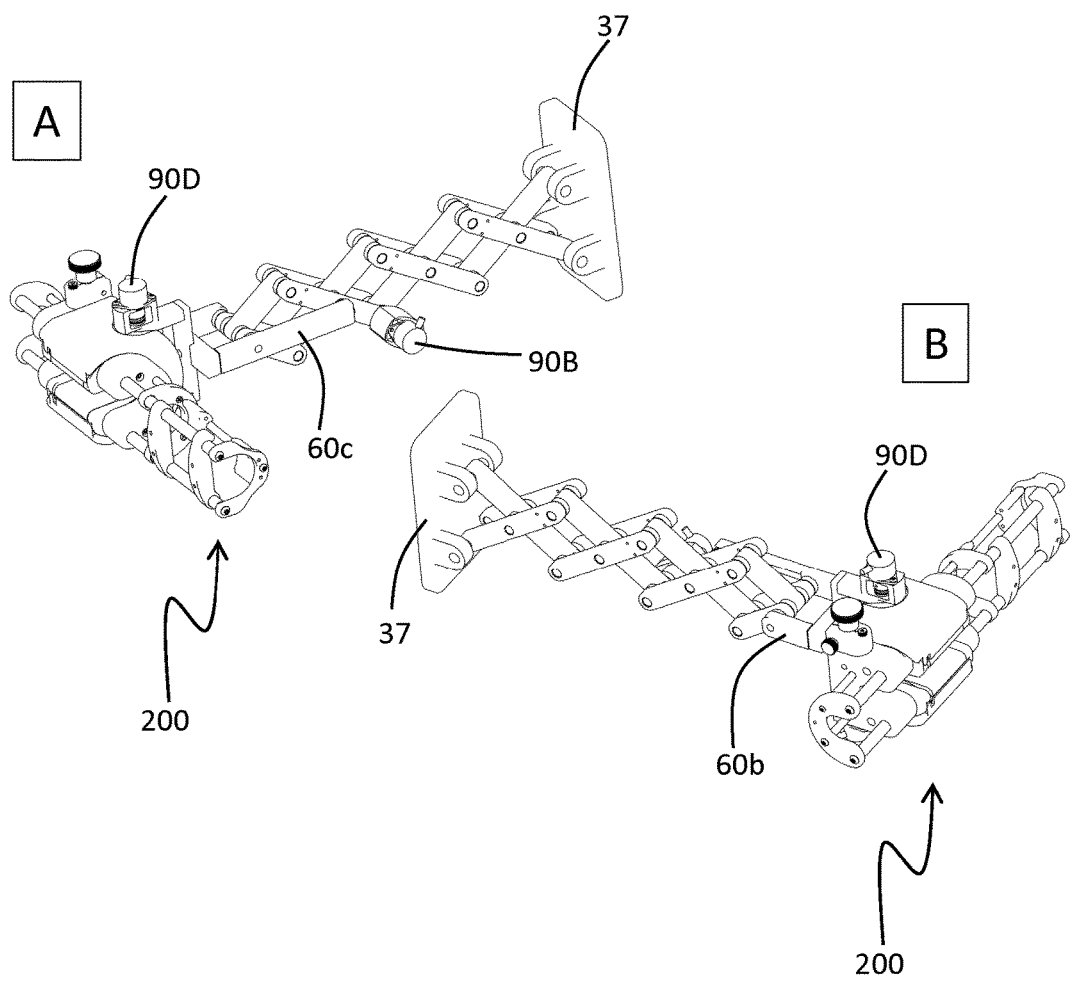
FIG. 7 shows (A) a first perspective view and (B) a second perspective view of a variant of the compound rotational interface and stepper combination shown in FIG. 3.

A single pivot coupling of the compound pinned parallelogram 32 to the interface base 36 to provide angular motion is optional. The compound pinned parallelogram structure may be coupled with two parallelogram linkage bars pivotally coupled to the base, for example as shown in FIG. 7. One of the two pivot couplings may also be slidable along base 37 in a lateral direction transverse to the longitudinal axis of the compound pinned parallelogram 32. Double pivot coupling to the base 37 can remove the need for a counterbalance mechanism 70 and rotational joint 62. However, it will be recognized that incorporation of the rotational motion of the compound pinned parallelogram is not inextricably coordinated with incorporation of a counterbalance mechanism or rotational joint 62, and that any one or two of these three elements may provide a benefit in the absence of the other(s).

Coupling of the compound pinned parallelogram 32 to rotational adaptor 34 may be varied. Instead of coupling to neighboring central pivot joints to asymmetric bracket 60 along a longitudinal axis of the compound pinned parallelogram, coupling could be achieved with a lateral bar pivotally coupled to opposing laterally aligned peripheral pivot joints of the distal end of the compound pinned parallelogram, with one of the pivot couplings being slidable in a lateral direction. However, a disadvantage of lateral coupling, as compared to longitudinal coupling, to the distal end of the compound pinned parallelogram may be lateral motion as the compound pinned parallelogram collapses/extends as well as potential friction from lateral sliding given that the lateral sliding motion is normal or perpendicular to the linear expanding/collapsing motion axis of the compound pinned parallelogram. In another example of a modification of the coupling of the compound pinned parallelogram 32 to rotational adaptor 34, asymmetric U-bracket 60 may be substituted with a symmetric U-bracket in which each of two parallel arms of the symmetric U-bracket is coupled to two consecutive central pivot joints (for example central pivot joints 50b and 50c shown in FIG. 2) along a longitudinal axis of the compound pinned parallelogram, each of the two parallel arms of the symmetric U-bracket pivotally coupled to an end or distal central pivot joint (e.g., distal central pivot joint 50b) and slidably coupled to a neighboring central pivot joint (e.g., central pivot joint 50c).

Figure 8:
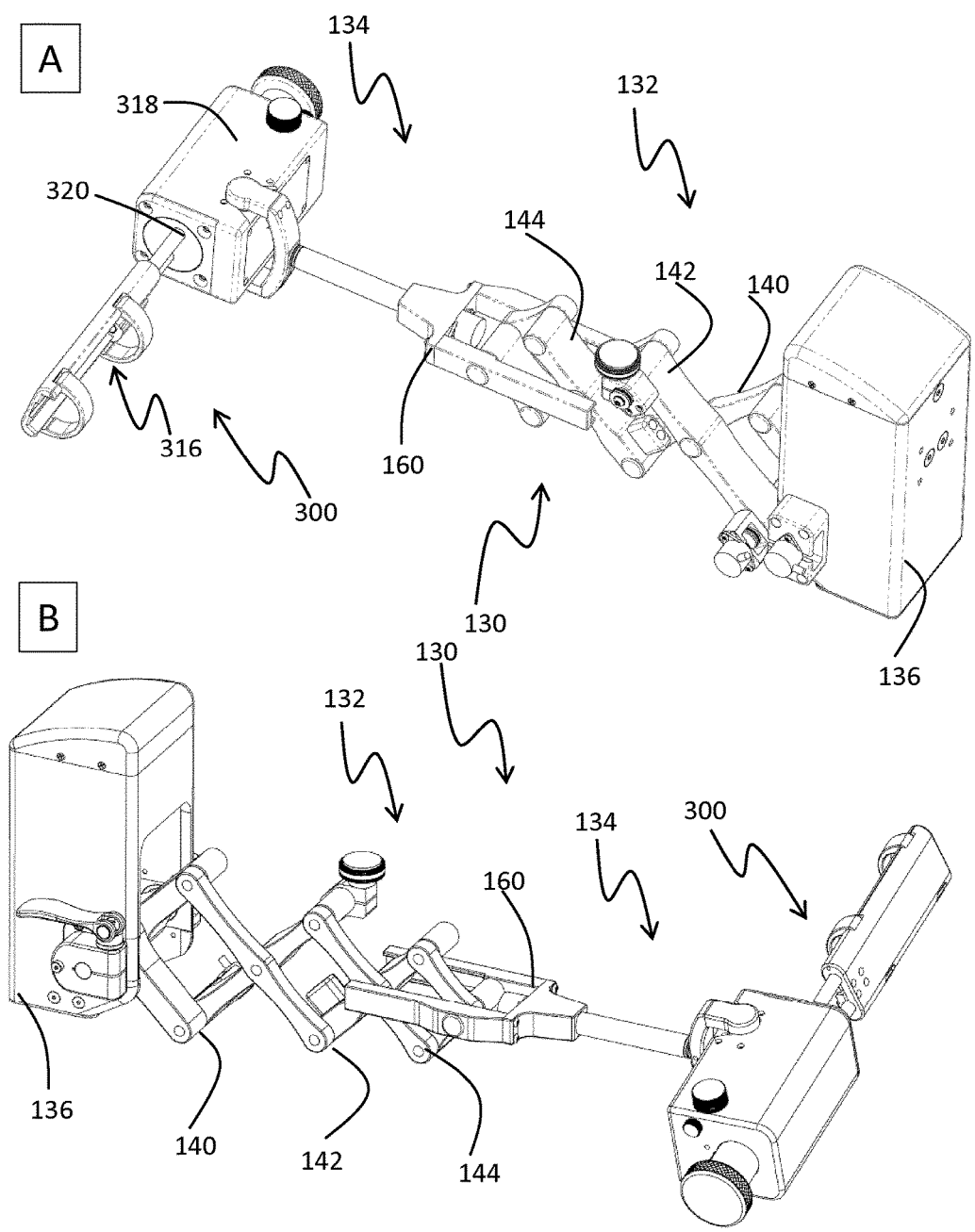
FIG. 8 shows (A) a first perspective view and (B) a second perspective view of another variant of the compound rotational interface and stepper combination shown in FIG. 3.
Figure 9:
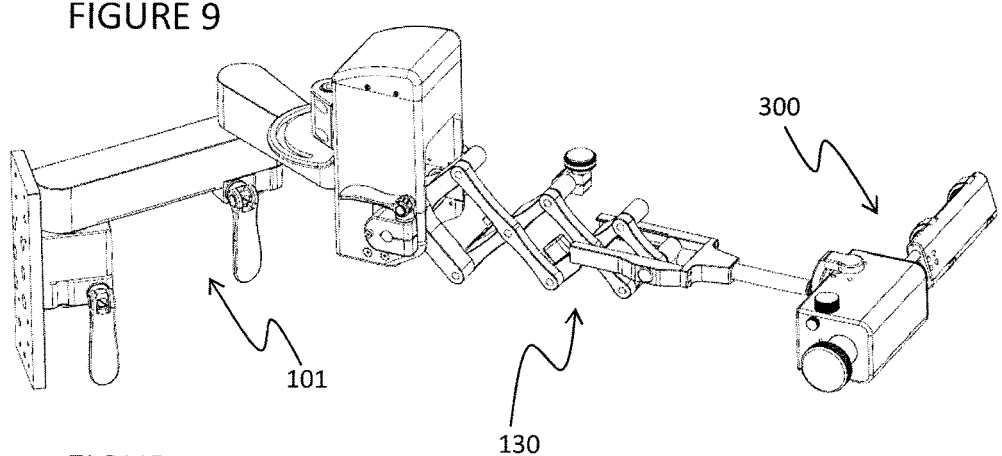
FIG. 9 shows a perspective view of the compound rotational interface and stepper combination shown in FIG. 8 coupled to a stabilizer.

Replacement of asymmetric U-bracket 60 with symmetric U-bracket 160 as well as further variation of the stepper and compound rotational interface assembly shown in FIG. 3 is illustrated in FIG. 8. FIG. 8 shows the structural difference between asymmetric U-bracket 60 and symmetric U-bracket 60 in that both parallel arms of the symmetric U-bracket 160 are pivotally connected to a first pivot joint, and both are slidably connected to a second pivot joint. The first pivot joint is an end pivot joint of a parallelogram linkage, while the second pivot joint is a neighboring pivot joint that is longitudinally aligned with the first pivot joint.

FIG. 8 shows a perspective view of a variant stepper 300 connected to a variant compound rotational interface 130. The compound rotational interface 130 comprises a compound pinned parallelogram 132 in a linearly expanding/ collapsing scissor arm arrangement linked to a rotational adaptor 134. The compound pinned parallelogram 132 connects to an interface base 136 that may be reversibly connected to a stabilizer, for example reversible connection to stabilizer 101 shown in FIG. 10. The compound pinned parallelogram 32 extends from the interface base 136 and links to rotational adaptor 134 which in turn links to stepper 300.

The compound pinned parallelogram 132 comprises three consecutively pinned parallelograms extending from an interface base 136, proximal parallelogram 140, intermediate parallelogram 142, and distal parallelogram 144, with proximal parallelogram 140 connected to the interface base 136, distal parallelogram 144 connected to the rotational adaptor 134, and intermediate parallelogram 142 connected to both the proximal parallelogram 140 and the distal parallelogram 144. Each parallelogram comprises four bars coupled at four corners by a pivot joint, with at least one pivot joint shared with an adjacent parallelogram unit. Each parallelogram is positioned to have two opposing corners aligned with the longitudinal dimension of the compound pinned parallelogram and two opposing corners aligned with the lateral dimension of the compound pinned parallelogram. Compound pinned parallelogram 132 is a variant of compound pinned parallelogram 32 and differs in that each of the pivot joints of compound pinned parallelogram 132 pivotally connects two bars, while compound pinned parallelogram 32 comprises pivot joints (for example, pivot joints 50, 52 and 54) that each pivotally connect three bars, first and second parallel bars and a third transverse bar. Compound pinned parallelogram 132 also differs in that bar/side length or perimeter lengths of the parallelogram units are not uniform. The perimeter length or the bar/side lengths of the parallelogram units progressively decrease from the end of the compound pinned parallelogram 132 connected to base 136 to the end connected to rotational adaptor 134 such that perimeter of parallelogram unit 140 is greater than the perimeter of parallelogram unit 142, and in turn the perimeter of parallelogram 142 is greater than the perimeter of parallelogram 144.

Variant stepper 300 differs from stepper 200 in that the roll axis of stepper 300 is provided by a revolute joint formed by cylinder block 320 (centrally located along the longitudinal dimension of carriage 316) rotationally received within a full pipe channel formed within base block 318 of stepper 300, while the corresponding roll axis of stepper 200 is provided by mating of semi-cylinder block 220 with a half-pipe channel formed in base block 218.

The number of parallelogram units within a compound pinned parallelogram may be varied as desired to suit a particular application. A compound parallelogram is generally recognized as comprising two connected and interacting parallelogram four-bar linkage units as described for example in U.S. Pat. No. 4,567,782 (issued 4 Feb. 1986), U.S. Pat. No. 5,569,013 (issued 29 Oct. 1996), and U.S. Pat. No. 5,984,408 (issued 16 Nov. 1999), and International PCT Publication No. WO/2016/112452 (published 21 Jul. 2016). As such a compound pinned parallelogram includes at least two parallelogram units. The compound pinned parallelogram may include two or more parallelogram units including for example, two units, three units, four units, five units, six units or more as needed by a desired range of motion or to suit desired parameters of a particular implementation. One or both of ends of the compound pinned parallelogram may be configured with partial parallelogram structures as needed to connect to a base and/or rotational adaptor for connection to the stepper.

The compound pinned parallelogram may be replaced with other parallelogram linkages such as a single parallelogram unit, a single pinned parallelogram unit, or multiple serially connected parallelogram units in implementations where the removal of structural benefits of the compound pinned parallelogram can be accommodated. FIG. 10 provides a schematic for comparison of features of a single parallelogram unit, a single pinned parallelogram unit, a compound parallelogram and a compound pinned parallelogram. A single parallelogram unit 502 provides a single DOF with one side and two pivot joints connected to base 500. A single pinned parallelogram unit 504 provides two DOF with a single pivot joint connected to base 500. A compound parallelogram 506 comprises multiple serially connected parallelogram units with first and second adjacent parallelogram units, 506a and 506b, sharing a common side. A compound pinned parallelogram 508 comprises multiple connected pinned parallelogram units with first and second adjacent parallelogram units, 508a and 508b, sharing a common corner or pivot joint.

A counterbalance mechanism is optional as shown for example in FIG. 7. Furthermore, a counterbalance mechanism may be replaced with a counterweight mechanism. When a counterbalance mechanism is used the counterbalance mechanism may be any conventional mechanism including gas springs, mechanical coiled springs, hydraulic springs and the like.

The compound rotational interface need not comprise a dedicated handle for manual control of the motion of the rotatable joint as control may be motorized. Furthermore, for manual control a handle may be located on a stepper and/or the compound rotational interface.

The compound rotational interface need not include brakes or locking mechanisms. For example, one or both of first brake 80 and second brake 82 shown in FIG. 2 may be removed while still providing a workable and operable compound rotational interface.

The use of encoders to track the orientation of the compound rotational interface is optional. When encoders are incorporated any conventional encoder may be used including optical encoders or magnetic encoders. The encoders provide a significant benefit for tracking and monitoring position of an instrument held by the stepper such as an ultrasound probe. A particular example of this benefit may be in a multi-modality MM to ultrasound co-registered targeted prostate biopsy. Furthermore, encoder tracking can provide a method for detection and differentiation of unintended patient movement from intended motion of the stepper directed by the physician, where unintended patient movement is indicated by activation of encoders 90D and 90C either individually or in combination, with a simultaneous absence or lack of activation or relatively lesser activation from one or more of other encoders coupled to the compound rotational interface and the stepper.

The compound rotational interface may be used in combination with software (used interchangeably with computer programmable code) used to receive and analyze encoder data or data from any other mechanism of positional tracking and output and optionally graphically display positional information of a corresponding medical device. Taking TRUS imaging as an example, software may be designed to display a 2D live video received from commercially available ultrasound machines and use this 2D video to reconstruct a 3D ultrasound image volume. A system comprising an encoder equipped compound rotational interface and stepper with software and associated computer hardware can be designed to work with clinicians' existing ultrasound machines, transrectal ultrasound (TRUS) probes, commercially available needles, needle guides/templates and needle gun combination. Additional software features include patient data management, multi-planar reconstruction, segmentation, image measurements and 3D image registration.

Encoders in the stepper and compound rotational interface send position information to a computer workstation, allowing it to track probe position and orientation. This may be done through the use of a kinematic chain. A look up table of positions is used to calculate the end position of the tracker arm. A look up table facilitates analysis, as a precise mathematical representation of the kinematics of the compound rotational interface is difficult to determine due to complex geometry of the joints employed. Mathematical equations representing the geometry of the stepper allow calculation of the end position of the probe given the end position of the compound rotational interface.

Control of the ultrasound probe and ultrasound system may be done manually by the physician, just as it would be performed in the absence of computer software representation of positional information. However, by tracking the position and orientation of the ultrasound probe while capturing the video image, the computer workstation is able to generate a 3D volume from a series of live 2D ultrasound images, display a 3D image and 3D rendered surface model of the prostate, and display the live image position within the prostate.

The computer workstation is connected to the ultrasound system via a cable and hardware device that converts the real-time video stream 2D ultrasound image into a format that is readable by the system software. The reconstructed 3D image stack can be marked up with gland segmentation or other markers. Previously-acquired images of the patient's prostate can be registered to this 3D stack, based on the principle that features of the prostate can be visualized consistently with a number of imaging modalities.

The physician may attach a commercially available biopsy needle guide to the TRUS probe and use the probe and biopsy needle to perform the prostate biopsy procedure. During the biopsy procedure this real-time 2D ultrasound image is visible on the computer display. This 2D live ultrasound image can be marked up to record the locations where the biopsies were acquired during the procedure. As the probe and needle guide are maneuvered by the physician, the position and orientation of the probe is tracked. Needle trajectory is estimated by the software based on positional data inputs and can be shown relative to the 3D image stack. This information is provided so the physician can assess prostate abnormalities, plan, and implement biopsy procedures.

Data, notes and images are stored in the patient file for later retrieval. Images may be stored in memory as unchanged originals. Image mark-ups may be stored in memory in any convenient format (e.g., DICOM format) with the same image size and orientation as the 3D ultrasound stack. Measures can be put in place to protect against data loss. This includes file transfer where data loss is evaluated upon receipt and/or reading of data.

The software may be used to detect unintended patient movement. Furthermore, once unintended patient motion is detected, the software may compensate positional representations to adjust for unintended patient motion. Patient motion compensation is based on detection of motion profiles provided by encoders that are different when the movement is intentional vs unintentional. For example, the encoders in the rotational adaptor may be activated when the patient moves, but the encoders of the parallelogram linkage do not move or move less than a predetermined threshold level. This is because the patient's sphincter provides coupling between the probe and the prostate. When the physician is moving the probe intentionally, the encoders in the parallelogram linkage move. The software applies a transform to the tracking which negates the unintentional movement when it is detected. This is facilitated the mechanical tracking of 6 degrees of freedom, allowing processing of encoder data for the 6 degrees of freedom individually and in any combination.

The compound rotational interface may optionally include any type of calibrated indicia to mark the orientation of the compound pinned parallelogram or any rotational joint.

The rotational interface may include structures that limit linear or angular motion of the compound rotational interface, for example to a desired range of motion such as 180 degrees or 90 degrees or 45 degrees depending on an application.

The compound rotational interface may be operated by manual manipulation or parts or all of the motion of the compound rotational interface may be actuated by automated or robotic control.

The compound rotational interface will define at least one axis of rotation that is maintained in a substantially perpendicular orientation to the longitudinal axis of an elongate medical instrument held in the stepper. The axis of rotation may be either a yaw axis or a pitch axis when a pivot joint is incorporated in the compound rotational interface. When a ball joint is incorporated in the rotational interface, the ball joint may be configured to provide both a yaw axis and a pitch axis. Similarly, when a dual-axis gimbal joint is incorporated in the rotational interface, the dual-axis gimbal joint may be configured to provide both a yaw axis and a pitch axis. The combination of rotational joints 62 and 66 is an example of an extended dual-axis gimbal joint.

The compound rotational interface may be incorporated into most conventional stabilizer/stepper assemblies. With respect to TRUS systems, incorporating the rotational interface may benefit operation of many different types and techniques of ultrasound imaging, biopsy and/or therapy. For example, the rotational interface may benefit both side-fire and end-fire transducers. Other examples of ultrasound transducer setups include high-intensity focused ultrasound (HiFU), an ultrasound transducer with a spectroscopy camera at its tip, electromagnetic acoustic imaging (EMAI) where radiofrequency electromagnetic waves are used to induce ultrasound emission from a target tissue, or a dual mode ultrasound/EMAI transducer, or a multi-modality MRI to Ultrasound co-registered targeted prostate biopsy.

Embodiments described herein are intended for illustrative purposes without any intended loss of generality. Still further variants, modification and combinations thereof are contemplated and will be recognized by the person of skill in the art. Accordingly, the foregoing detailed description and accompanying drawings are not intended to limit scope, applicability, or configuration of claimed subject matter.

What is claimed is:

1. A stabilizer and stepper assembly for performing a medical procedure, the assembly comprising:
   a stabilizer comprising a plurality of stabilizer joints supporting multi-directional motion;
   a stepper for holding an elongate medical instrument having a longitudinal axis, the stepper supporting linear, rotational or both linear and rotational motion of the medical instrument on its longitudinal axis;
   a compound rotational interface operably connected to the stabilizer and the stepper;
   the compound rotational interface comprising a compound pinned parallelogram in a scissor arm arrangement bound by a first end coupled to the stabilizer and a second end coupled to a first rotational joint of the compound rotational interface, the first rotational joint coupled to the stepper, rotation of the stepper relative to the compound pinned parallelogram provided on an axis of rotation defined by the first rotational joint;
   the compound pinned parallelogram moveable from a first linear position to a second linear position and the first rotational joint moveable from a first angular position to a second angular position; and
   a linear direction defined by the compound pinned parallelogram substantially perpendicular to the axis of rotation defined by the first rotational joint, and the axis of rotation substantially perpendicular to the longitudinal axis of the medical instrument.

2. The assembly of claim 1, further comprising a second rotational joint of the compound rotational interface, the second rotational joint coupling the second end of the compound pinned parallelogram to the first rotational joint, rotation of the first rotational joint relative to the compound pinned parallelogram provided on an axis of rotation defined by the second rotational joint, the axis of rotation defined by the second rotational joint substantially perpendicular to the axis of rotation defined by the first rotational joint and substantially parallel to the linear direction.

3. The assembly of claim 2, further comprising a second motor for automated control of the motion of the second rotational joint.

4. The assembly of claim 2, wherein the second rotational joint is coupled to the second end of the compound pinned parallelogram with a U-bracket coupled to a second pivot joint of the compound pinned parallelogram and a third pivot joint of the compound pinned parallelogram, the second and third pivot joints being two neighboring pivot joints along the linear direction of the compound pinned parallelogram.

5. The assembly of claim 1, wherein the compound pinned parallelogram supports rotational motion and is moveable from a first angular position to a second angular position on a first pivot joint of the compound pinned parallelogram located proximal to the first end of the compound pinned parallelogram, the first pivot joint defining an axis of rotation substantially perpendicular to the linear direction.

6. The assembly of claim 5, wherein the first pivot joint located proximal to the first end is supported by a counterbalance mechanism.

7. The assembly of claim 5, further comprising a second brake coupled to the first pivot joint located proximal to the first end to reversibly lock rotational motion of the compound pinned parallelogram.

8. The assembly of claim 1, further comprising a first brake coupled to the compound pinned parallelogram to reversibly lock motion in the linear direction.

9. The assembly of claim 1, further comprising a first motor for automated control of the motion of the first rotational joint.

10. The assembly of claim 1, wherein the compound rotational interface further comprises at least two encoders, a first encoder for tracking motion of the compound pinned parallelogram and a second encoder for tracking motion of the first rotational joint.

11. The assembly of claim 1, wherein the compound pinned parallelogram comprises at least three parallelogram units.

12. The assembly of claim 1, wherein the linear direction of the compound pinned parallelogram is substantially aligned with the center of gravity of the stepper.

13. The assembly of claim 1, wherein the linear direction is substantially perpendicular to the longitudinal axis of the medical instrument when the first rotational joint is held at a center of its range of motion.

14. The assembly of claim 1, wherein the stepper holds the elongate medical instrument.

15. A compound rotational interface and stepper assembly, the assembly comprising:
   a stepper holding an elongate medical instrument having a longitude axis, the stepper supporting linear, rotational or both linear and rotational motion of the elongate medical instrument on the longitudinal axis;
   a compound rotational interface comprising a compound pinned parallelogram in a scissor arm arrangement bound by a first end coupled to a base and a second end coupled to a first rotational joint of the compound rotational interface, the first rotational joint coupled to the stepper, rotation of the stepper relative to the compound pinned parallelogram provided on an axis of rotation defined by the first rotational joint;
   the compound pinned parallelogram moveable from a first linear position to a second linear position and the first rotational joint moveable from a first angular position to a second angular position; and
   a linear direction defined by the compound pinned parallelogram substantially perpendicular to the axis of rotation defined by the first rotational joint.

16. The assembly of claim 15, further comprising a second rotational joint of the compound rotational interface, the second rotational joint coupling the second end of the compound pinned parallelogram to the first rotational joint, rotation of the first rotational joint relative to the compound pinned parallelogram provided on an axis of rotation defined by the second rotational joint, the axis of rotation defined by the second rotational joint substantially perpendicular to the axis of rotation defined by the first rotational joint and substantially parallel to the linear direction.

17. The assembly of claim 16, wherein the second rotational joint is coupled to the second end of the compound pinned parallelogram with a U-bracket coupled to a second pivot joint of the compound pinned parallelogram and a third pivot joint of the compound pinned parallelogram, the second and third pivots joints being two neighboring pivot joints along the linear direction of the compound pinned parallelogram.

18. The assembly of claim 15, wherein the compound pinned parallelogram supports rotational motion and is moveable from a first angular position to a second angular position on a first pivot joint of the compound pinned parallelogram, the first pivot joint coupling the first end of the compound pinned parallelogram to the base, the first pivot joint defining an axis of rotation substantially perpendicular to the linear direction.

19. The assembly of claim 18, wherein the first pivot joint at the first end is supported by a counterbalance mechanism.

20. The assembly of claim 15, further comprising a brake coupled to the compound pinned parallelogram.

21. The assembly of claim 15, wherein the compound rotational interface further comprises at least two encoders, a first encoder for tracking motion of the compound pinned parallelogram and a second encoder for tracking motion of the first rotational joint.

22. The assembly of claim 15, wherein the compound pinned parallelogram comprises at least three parallelogram units.

23. The assembly of claim 15, wherein the linear direction of the compound pinned parallelogram is substantially aligned with the center of gravity of the stepper.

* * * * *